(12) United States Patent
Holland et al.

(10) Patent No.: US 9,675,820 B2
(45) Date of Patent: Jun. 13, 2017

(54) ULTRASOUND-MEDIATED INDUCEMENT, DETECTION, AND ENHANCEMENT OF STABLE CAVITATION

(71) Applicant: University of Cincinnati, Cincinnati, OH (US)

(72) Inventors: Christy K. Holland, Cincinnati, OH (US); Saurabh Datta, Cincinnati, OH (US); T. Douglas Mast, Cincinnati, OH (US); Nikolas Ivancevich, Cincinnati, OH (US); Kathryn Elizabeth Hitchcock, Cincinnati, OH (US); Kevin Haworth, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 15/008,821

(22) Filed: Jan. 28, 2016

(65) Prior Publication Data

US 2016/0144203 A1 May 26, 2016

Related U.S. Application Data

(62) Division of application No. 13/257,657, filed as application No. PCT/US2010/027992 on Mar. 19, 2010, now abandoned.

(Continued)

(51) Int. Cl.
*A61N 7/00* (2006.01)
*A61B 8/06* (2006.01)
(Continued)

(52) U.S. Cl.
CPC ............... *A61N 7/00* (2013.01); *A61B 8/06* (2013.01); *A61B 8/0808* (2013.01); *A61B 8/481* (2013.01);
(Continued)

(58) Field of Classification Search
CPC ...... A61B 17/2202; A61B 2017/00172; A61B 2017/0019; A61B 2017/00194;
(Continued)

(56) References Cited

U.S. PATENT DOCUMENTS 6,575,922 B1   6/2003 Fernside et al.
2003/0153077 A1   8/2003 Pitt et al.
(Continued)

FOREIGN PATENT DOCUMENTS

| EP | 0351610 A2 | 6/1989 |
| WO | 2008062342 | 5/2008 |
| WO | 2008157422 | 12/2008 |

OTHER PUBLICATIONS

Office Action for corresponding Canadian Application No. 2,756,038 dated Jan. 11, 2017.

*Primary Examiner* — Ruth S Smith
(74) *Attorney, Agent, or Firm* — Dinsmore & Shohl LLP

(57) ABSTRACT

Methods and systems for passively detecting stable cavitation and enhancing stable cavitation during sonothrombolysis are provided. The method of passively detecting stable cavitation includes providing a determined level of ultrasonic energy and detecting a scattered level of ultrasonic energy. The system for inducing and passively detecting stable cavitation includes a dual-element annular transducer array configured to provide a fundamental ultrasonic frequency and to detect an ultrasonic frequency that is a derivative of the fundamental frequency. The method of enhancing stable cavitation includes administering a nucleating agent and a thrombolytic agent to a treatment zone, providing a determined level of ultrasonic energy, and detecting a scattered level of ultrasonic energy.

16 Claims, 9 Drawing Sheets

Related U.S. Application Data

(60) Provisional application No. 61/162,061, filed on Mar. 20, 2009.

(51) Int. Cl.
  *A61B 8/08* (2006.01)
  *G01S 7/52* (2006.01)
  *A61M 37/00* (2006.01)
  *A61B 17/22* (2006.01)
  *A61B 17/00* (2006.01)

(52) U.S. Cl.
  CPC .. *A61B 17/2202* (2013.01); *A61B 2017/0019* (2013.01); *A61B 2017/00172* (2013.01); *A61B 2017/00194* (2013.01); *A61B 2017/22008* (2013.01); *A61B 2017/22088* (2013.01); *A61M 37/0092* (2013.01); *A61N 2007/0039* (2013.01); *G01S 7/52038* (2013.01)

(58) Field of Classification Search
  CPC A61B 2017/22008; A61B 2017/22088; A61B 8/06; A61B 8/0808; A61B 8/481; A61M 37/0092; A61N 2007/0039; A61N 7/00; G01S 7/52038
  See application file for complete search history.

(56) References Cited

U.S. PATENT DOCUMENTS

| | | |
|---|---|---|
| 2007/0161902 A1 | 7/2007 | Dan |
| 2009/0098212 A1* | 4/2009 | Fossheim ............ A61K 9/1271 424/502 |
| 2010/0056924 A1 | 3/2010 | Powers |

* cited by examiner

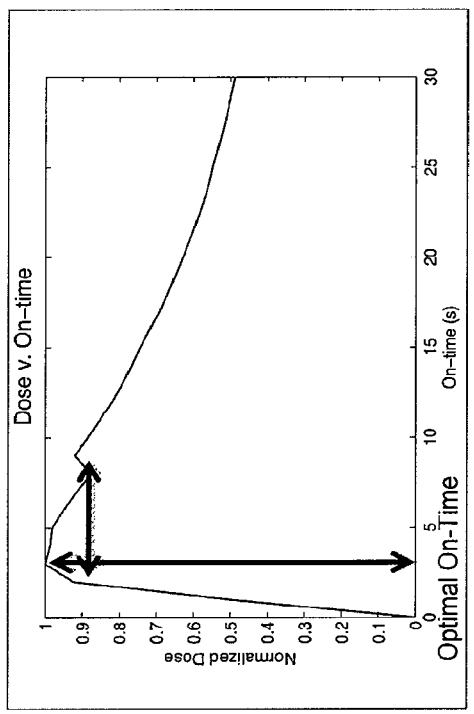
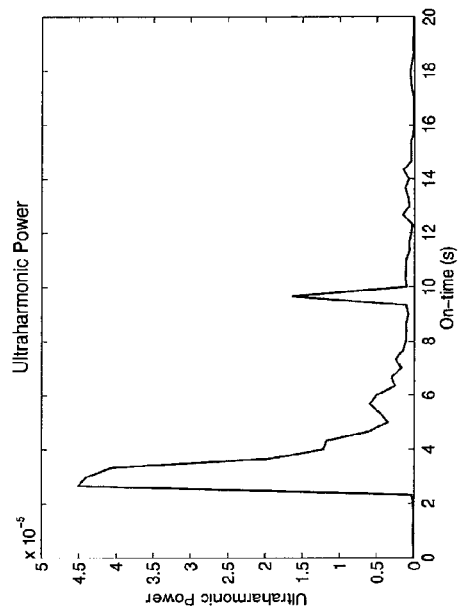
FIG. 8

ULTRASOUND-MEDIATED INDUCEMENT, DETECTION, AND ENHANCEMENT OF STABLE CAVITATION

This application is a divisional application of U.S. application Ser. No. 13/257,657, filed on Feb. 27, 2012, which claims priority to Int'l Application No. PCT/U.S.2010/027992, filed on Mar. 19, 2010, which claims priority to U.S. Provisional Application Ser. No. 61/162,061, filed Mar. 20, 2009, the contents of which are hereby incorporated by reference in their entirety.

TECHNICAL FIELD

The present invention relates to methods and systems of inducing, detecting, and enhancing stable cavitation using ultrasound. More specifically, the present invention relates to methods and systems of inducing, passively detecting, and enhancing stable cavitation during sonothrombolysis.

BACKGROUND

Due to the prevalence of thrombo-occlusive disease worldwide and the need for improved clinical treatments, ultrasound has been investigated, either alone or in combination with thrombolytic drugs, to improve recanalization in patients with this disease. A common thrombo-occlusive disease is ischemic stroke, whereby a clot within a vessel in the brain interrupts blood supply to the brain tissue. The occurrence of ischemic strokes is widespread, with greater than seven hundred thousand occurrences within the United States each year. Ischemic strokes occur as a result of a loss of blood supply to a portion of the brain which may be caused by thrombosis, embolism, or hypoperfusion. Ischemic strokes can lead to a variety of physical complications including permanent neurological damage and death. When brain tissue is deprived of oxygen for more than 60-90 seconds, the brain tissue loses its function; when brain tissue is deprived of oxygen for greater than three hours, irreversible injury results, leading to infarction. Thus, the ability to promptly treat a stroke is critical to the survival of a patient suffering from ischemic stroke.

Currently, treatment of ischemic stroke is generally limited to thrombolytic therapies, whereby a blood clot is broken up or dissolved. The American Heart Association recommends the administration of the thrombolytic agent tissue plasminogen activator ("t-PA") for the treatment of ischemic strokes. However, this therapy possesses a number of drawbacks. For example, the administration of recombinant tissue plasminogen activator ("rt-PA") is only moderately efficacious, resulting in a 30% greater chance of little or no disability in rt-PA treated patients as compared to a control at 3 months. Further, there is a 6.4% incidence of intracerebral hemorrhage in patients receiving this thrombolytic therapy. Thus, there is a substantial need for improved therapies to treat ischemic strokes.

The addition of ultrasound with clinically relevant intensities and frequencies has been shown to enhance the rate of some thrombolytic therapies in vitro. Moreover, a correlation has recently been observed between stable cavitation and ultrasound-enhanced thrombolysis. Cavitation is the formation, oscillation, and/or collapse of gaseous and/or vapor bubbles in a liquid due to an acoustic pressure field. In particular, stable cavitation results in emissions at subharmonic and ultraharmonic frequencies of the main excitation frequency.

Currently, methods of detecting cavitation include a variety of techniques, including acoustic cavitation detection and optical cavitation detection. However, these detection methods are also limited. Further, detection methods have yet to be employed to enhance stable cavitation during sonothrombolysis. Thus, additional methods and systems for ultrasound-mediated inducement, detection, and enhancement of stable cavitation are needed.

SUMMARY OF THE INVENTION

In one embodiment, a system for inducing and passively detecting stable cavitation is provided, the system comprising a dual-element annular transducer array having a source transducer and a detector transducer, and an ultrasonic driver adapted to generate energy that can be converted at the source transducer to ultrasonic energy suitable for penetrating a treatment zone of a patient. The system is adapted to provide a determined level of ultrasonic energy and to receive a scattered level of ultrasonic energy substantially throughout the treatment zone of the patient, in which the source transducer provides an ultrasonic frequency that is a fundamental ultrasonic frequency, and the detector transducer receives an ultrasonic frequency that is a derivative frequency of the fundamental ultrasonic frequency selected from the group consisting of a subharmonic frequency, an ultraharmonic frequency, and combinations thereof.

In another embodiment, the present invention relates to a method for inducing and passively detecting stable cavitation during sonothrombolysis. The method comprises providing a determined level of ultrasonic energy substantially throughout a treatment zone of a patient and detecting a scattered level of ultrasonic energy. The determined level of ultrasonic energy is produced by a source transducer and comprises a fundamental ultrasonic frequency. The scattered level of ultrasonic energy is received by a detector transducer and comprises a derivative frequency of the fundamental ultrasonic frequency selected from the group consisting of a subharmonic frequency, an ultraharmonic frequency, and combinations thereof, wherein detection of the derivative frequency is indicative of stable cavitation during sonothrombolysis.

In still another embodiment, a method for enhancing stable cavitation during sonothrombolysis is provided, the method comprising administering a nucleating agent and a thrombolytic agent to a treatment zone of a patient and providing a determined level of ultrasonic energy substantially throughout the treatment zone of the patient. The determined level of ultrasonic energy is produced by a source transducer and comprises a fundamental ultrasonic frequency, wherein the determined level of ultrasonic energy is provided in intervals separated by rest periods, wherein substantially no ultrasonic energy is provided during rest periods, such that the intervals of the determined level of ultrasonic energy enhance stable cavitation during sonothrombolysis.

These and other features and advantages of these and other various embodiments according to the present invention will become more apparent in view of the drawings, detailed description, and claims provided herein.

BRIEF DESCRIPTION OF THE DRAWINGS

The following detailed description of the embodiments of the present invention can be better understood when read in conjunction with the following drawings, where like structure is indicated with like reference numerals, and in which:

FIG. 8 illustrates stable cavitation activity and a total cavitation dose versus ultrasound on-time (i.e. interval duration) in an ex vivo porcine carotid artery model with physiologic flows and pressures. Stable cavitation power decays as a function of time. By integrating the power signal in time over multiple pulses, the total 30 minute cavitation dose was calculated and the on-time that yielded the maximum cavitation dose was calculated. The system is operated with the on-time that provides the maximum cavitation dose, or at the center of the 90% width of the cavitation dose.

Figure 1:
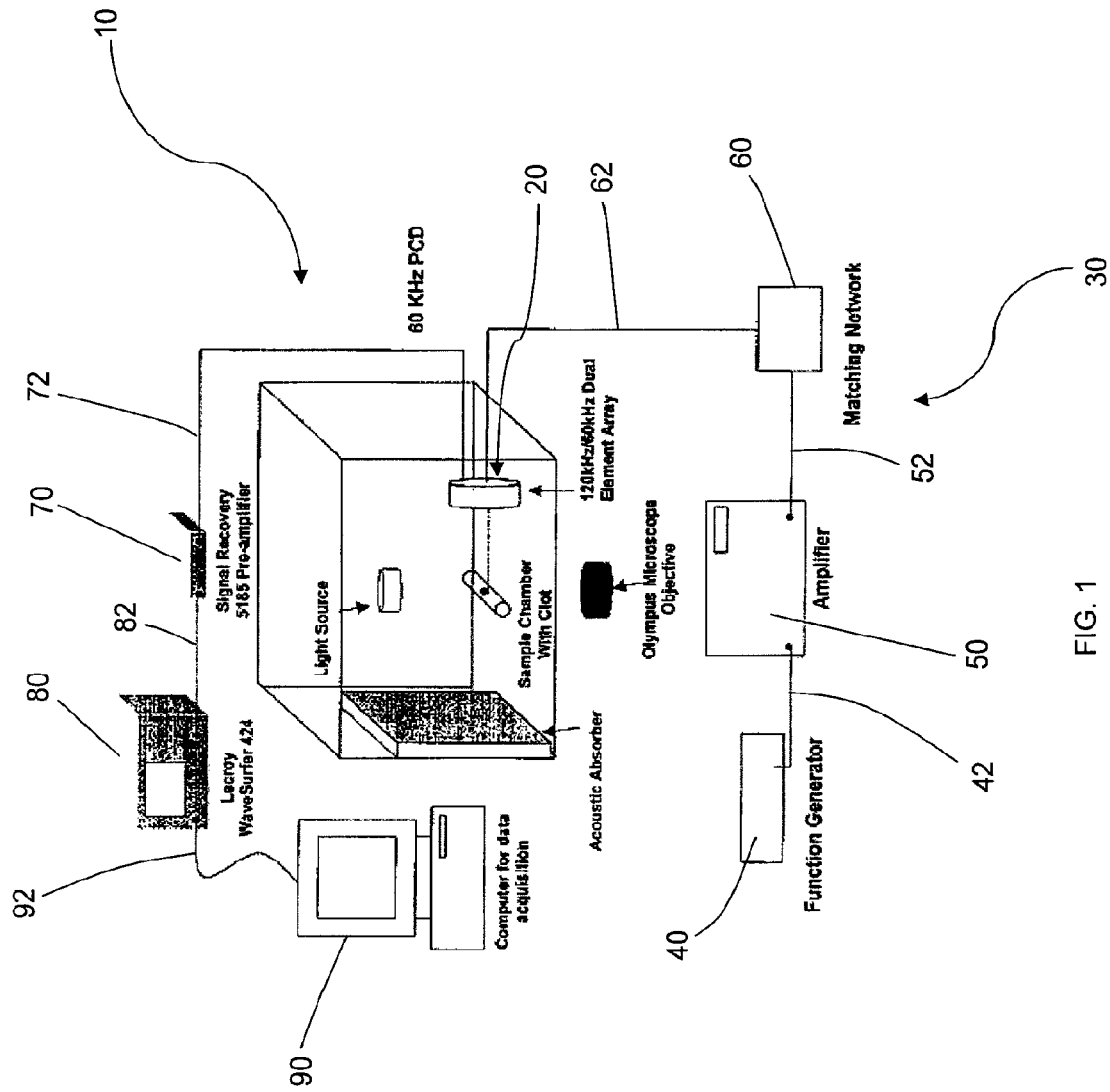
FIG. 1 is a schematic of an apparatus for inducing and passively detecting stable cavitation during ultrasound-enhanced thrombolysis experiments with video microscopy data acquisition.

Skilled artisans appreciate that elements in the figures are illustrated for simplicity and clarity and are not necessarily drawn to scale. For example, the dimensions of some of the elements in the figures may be exaggerated relative to other elements, as well as conventional parts removed, to help to improve understanding of the various embodiments of the present invention.

DETAILED DESCRIPTION OF THE INVENTION

The following terms are used in the present application:

In the context of stable cavitation, the terms "inducing" and "inducement" are used interchangeably herein to refer to the nucleation or initiation of stable cavitation.

In the context of passively detecting stable cavitation, the term "passively" is used herein to refer to receiving a signal with a transducer or hydrophone which is used exclusively to receive an emitted and/or scattered level of ultrasonic energy from acoustically activated bubbles. In the context of a system for inducing and passively detecting stable cavitation, the term "passive" is used herein to refer to a transducer and/or a hydrophone which is used exclusively to receive an emitted and/or scattered level of ultrasonic energy from acoustically activated bubbles.

The term "cavitation" is used herein to refer to the formation, oscillation, and/or collapse of gaseous and/or vapor bubbles in a liquid due to an acoustic pressure field. Cavitation is generally classified into two types: stable cavitation and inertial cavitation. The term "stable cavitation" is used herein to refer to a microbubble or nanobubble oscillating in an ultrasound field, whereby the predominant acoustic emissions occur not only at the fundamental ultrasonic frequency and harmonic frequency but also at the subharmonic and ultraharmonic frequencies. The origin of these emissions is a nonlinear standing wave, i.e. a Faraday wave, on the outer surface of the bubble, or nonlinear volumetric oscillations of the bubble during pulsation in the sound field. The term "inertial cavitation" is used herein to refer to cavitation which results in broadband emissions.

The term "thrombolysis" is used herein to refer to the dissolution or breaking up of a clot or thrombus. The term "sonothrombolysis" is used herein to refer to ultrasound-enhanced or ultrasound-mediated thrombolysis.

The term "determined level of ultrasonic energy" is used herein to refer to the ultrasound peak-to-peak pressure amplitude that is produced by a source transducer.

In the case of thrombolysis, the term "treatment zone" is used herein to refer to the area comprising a blood clot. In one embodiment, the treatment zone is part of a vascular model and comprises a blood clot. In another embodiment, the treatment zone is located within a mammalian subject and refers to the area surrounding and comprising a blood clot. In a specific embodiment, in the case of sonothrombolysis of a treatment zone, the term "treatment zone" is to the area encompassed by the −6 dB focal volume of the source transducer, which is confocally aligned with the −6 dB focal volume of the passive cavitation detector.

The term "source transducer" is used herein to refer to a transducer which produces a determined level of ultrasonic energy. The term "detector transducer" is used herein to refer to a transducer which receives a scattered level of ultrasonic energy.

The term "fundamental ultrasonic frequency", as used herein, refers to the frequency of ultrasonic energy generated by a source transducer producing pressure cycles per unit time. The fundamental ultrasonic frequency employed herein can range from about 100 kHz to about 10 MHz, or from about 100 kHz to about 2 MHz. In a very specific embodiment, the fundamental ultrasonic frequency is about 120 kHz.

When the fundamental ultrasonic frequency activates nano- or microbubbles, the bubbles scatter ultrasonic energy at a derivative frequency. Thus, the term "scattered level of ultrasonic energy" is used herein to refer to the pressure amplitude or the intensity of the ultrasound which is scattered from ultrasonically activated nano- and microbubbles.

The term "derivative frequency" is used herein to refer to any ultrasonic frequency or combination of ultrasonic frequencies scattered by bubbles undergoing stable cavitation. The derivative frequency is selected from a subharmonic frequency and/or an ultraharmonic frequency of the fundamental ultrasonic frequency applied to a treatment zone.

The term "harmonic frequency" is used herein to refer to integer multiples of the fundamental ultrasonic frequency. The term "subharmonic frequency" is used herein to refer to half the fundamental ultrasonic frequency. The detection of scattered subharmonic frequencies is indicative of stable cavitation. The term "ultraharmonic frequency" is used herein to refer to integer multiples of the subharmonic frequency, excluding integer multiples of the fundamental frequency. The detection of scattered ultraharmonic frequencies is also indicative of stable cavitation.

The term "dual-element annular transducer array" is used herein to refer to an array consisting of two transducer elements, wherein an annular element surrounds a central circular element. The term "single element transducer" is used herein to refer to a single element transducer that produces ultrasonic pressure waves. The term "linear array transducer" is used herein to refer to a multi-element transducer composed of a plurality of transducer elements. The transducer elements are electrically separate elements arranged along a line or curve. The term "two-dimensional array transducer" is used herein to refer to a matrix of transducer elements which provide beam control over a cross-sectional area. If the matrix is arranged in annuli, or concentric circles, the beam control provides spherical focusing at different depths from the face of the array. In the context of a transducer array, individual elements of the array may be square, hexagonal, annular, circular, or any other pattern which fills the emitting area of the transducer and can be controlled by a suitable driver system.

The term "Rayleigh distance" is used herein to refer to the natural focus of a transducer, that is, the location from the transducer face at which all the emitted waves are in phase. The "Rayleigh distance" employed herein can range from about 0.1 centimeters to about 30 centimeters, or from about 0.1 centimeters to 10 centimeters. As used herein, the terms "Rayleigh distance", "natural focus", and "focus" are interchangeable.

The term "hydrophone" is used herein to refer to a microphone configured to record and/or listen to ultrasound scattered by acoustically active bubbles.

The term "ultrasonic driver" is used herein to refer to a device having a radio frequency signal source and a power amplifier. Impedance matching circuitry between the power amplifier and transducer may optionally be employed to increase the efficiency of an ultrasonic driver.

The term "signal" is used herein to refer an electronic signal converted from a pressure wave in ultrasound. The hydrophone or detector transducer converts a pressure wave into a voltage signal as a function of time. The term "gated signal" is used herein to refer to a detected signal that is truncated in time such that only certain signals of the scattered level of ultrasonic energy are detected, and such that certain signals of the scattered level of ultrasonic energy are disallowed. The signals of the scattered level of ultrasonic energy that are detected are those that are emitted from a scattering source at a particular distance from the detector transducer.

The term "pre-amplifier" is used herein to refer to a device which prepares an electronic signal for recording and/or processing. The pre-amplifier circuitry may or may not be housed as a separate component. In the context of amplifying a signal, the term "amplifying" is used herein to refer to increasing the amplitude of the signal.

The term "digital oscilloscope" is used herein to refer to a device which converts measured voltages into digital information. Waveforms are sampled with an analog to digital converter at approximately two times the frequency of the highest frequency component of the observed signal. The samples are stored and accumulate until a sufficient amount are taken to describe the waveform. The signals are then reassembled for display. In the context of storing a signal, the term "storing" is used herein to refer to a data set that is stored in the memory of a microprocessor.

In the context of acquiring a signal, the term "acquiring" is used herein to refer to the process of sampling the voltage received by the detector transducer, hydrophone, or passive cavitation detector and converting the resulting samples into digital numeric values that can be manipulated by a computer. In the context of acquiring a signal with a computer, the term "data acquisition" is used herein to refer to the conversion of analog waveforms into digital values for processing on a computer.

The term "duty cycle" is used herein to refer to the pulse duration divided by the pulse repetition period. The duty cycle employed herein can range from about 0.01% to about 100%.

The term "bandwidth" is used herein to refer to the range of frequencies wherein the signal's Fourier transform has a power above about a quarter of the maximum value. In a specific embodiment, the bandwidth is about −6 dB. As used herein, the detector transducer is configured to receive a bandwidth centered at one or more subharmonic and/or ultraharmonic frequencies of the fundamental frequency.

The term "ultrasonic pressure amplitude" is used herein to refer to the peak-to-peak pressure amplitude. In one embodiment, the ultrasonic pressure amplitude employed herein can range from about 0.1 MPa to about 10.0 MPa, or from about 0.1 MPa to about 10.0 MPa.

In the context of stable cavitation, the term "enhanced" is used herein to refer to an increase in the number of ultrasonically activated bubbles or to an increase in the duration of bubble activity. The term "ultrasonically activated bubbles" is used herein to refer to bubbles with larger vibrational amplitude excursions. In the context of thrombolysis, the term "enhanced" is used herein to refer to an increase in lytic efficacy or to a reduced period of time for lytic effect. For example, in the context of thrombolysis, the percent clot mass lost in the presence of a predetermined level of ultrasound was greater than about 80% in the presence of a thrombolytic agent, a nucleating agent, and a determined level of ultrasound; whereas, in the presence of a thrombolytic agent and a nucleating agent (without ultrasound), the percent clot mass lost was less than about 35%. Thus, thrombolysis is enhanced in the presence of ultrasound, as compared with the absence of ultrasound.

The term "nucleating agent" is used herein to refer to an agent that initiates cavitation.

The term "thrombolytic agent" is used herein to refer to a therapeutic agent, such as a pharmaceutical, used in medicine to dissolve blood clots or thrombi in order to limit the damage caused by the blockage of the blood vessel.

The term "interval" is used herein to refer to continuous wave or pulsed wave ultrasound produced by a source transducer. The source transducer provides a determined level of ultrasonic energy in an interval. The term "interval duration" is used herein to refer to the period of time for which a determined level of ultrasonic energy is provided. In one embodiment, the interval duration employed herein can range from about 10 milliseconds to about 5 minutes, or from about 10 milliseconds to about 10 seconds.

The term "rest period" is used herein to refer to providing substantially no ultrasonic energy. The term "rest period duration" is used herein to refer to the period of time for which substantially no ultrasonic energy is provided. In one embodiment, the rest period duration employed herein can range from about 1 second to about 5 minutes, or from about 1 second to about 20 seconds.

The term "continuous wave ultrasound" is used herein to refer to a technique in which a transducer continuously emits ultrasound, wherein the ultrasound is varied sinusoidally.

The term "pulsed wave ultrasound" is used herein to refer to a technique in which a transducer emits ultrasound in pulses or tone bursts.

In the context of enhancing stable cavitation, the term "adjusting the determined level of ultrasonic energy" is used herein to refer to increasing or decreasing the peak-to-peak pressure output of the source transducer.

The term "passive cavitation detector" is used herein to refer to a transducer or a hydrophone which receives a scattered level of ultrasound from acoustically active bubbles. The term "transducer array" is used herein to refer to a transducer array which receives a scattered level of ultrasound from acoustically active bubbles. In one embodiment, the transducer array is a passive transducer array.

The term "nanobubble" is used herein to refer to bubbles on the size scale of nanometers. The term "microbubble" is used herein to refer to bubbles on the size scale of micrometers.

The term "ultrasound contrast agent" is used herein to refer to gas-filled vesicles (containing nanobubbles or microbubbles), which are administered, for example, intravenously to the systemic circulation to increase echogenicity on an ultrasound image.

The term "protective material" is used herein to refer to a protein, lipid or surface active agent which prevents dissolution of an entrapped bubble.

The term "liposome" is used herein to refer to microscopic vesicle consisting of a core enclosed by one or more phospholipid layers, wherein hydrophobic compounds and/or hydrophilic compounds can be contained within the core. The term "echogenic liposome" is used herein to refer to a liposome which produces an echo when exposed to ultrasound.

The term "beamwidth" is used herein to refer to the spatial extent of the ultrasound beam at the focus, natural focus, or Rayleigh distance of a transducer. In one embodiment, the beamwidth is about −6 dB, such that the pressure output is at least a quarter of the peak value (−6 dB beamwidth). The "beamwidth" can be controlled by changing the diameter or aperture of the transducer while keeping the frequency fixed. The beamwidth at the Rayleigh distance is about half of the diameter of the transducer. The beamwidth employed herein can range, for example, from about 0.1 centimeters to about 10 centimeters.

The terms "stable cavitation dose" and "dose" are used interchangeably herein to refer to the cumulative amount of acoustic energy detected that is directly attributed to non-linear bubble activity generating at a subharmonic frequency, an ultraharmonic frequency, and/or combinations thereof.

Embodiments of the present invention relate to ultrasound-mediated methods and systems of detecting and enhancing stable cavitation. In one embodiment, a system for inducing and passively detecting stable cavitation is provided, the system comprising a dual-element annular transducer array having a source transducer and a detector transducer, and an ultrasonic driver adapted to generate energy that can be converted at the source transducer to ultrasonic energy suitable for penetrating a treatment zone of a patient. The system is adapted to provide a determined level of ultrasonic energy and to receive a scattered level of ultrasonic energy substantially throughout the treatment zone of the patient, in which the source transducer provides an ultrasonic frequency that is a fundamental ultrasonic frequency, and the detector transducer receives an ultrasonic frequency that is a derivative frequency of the fundamental ultrasonic frequency selected from the group consisting of a subharmonic frequency, an ultraharmonic frequency, and combinations thereof.

Figure 2:
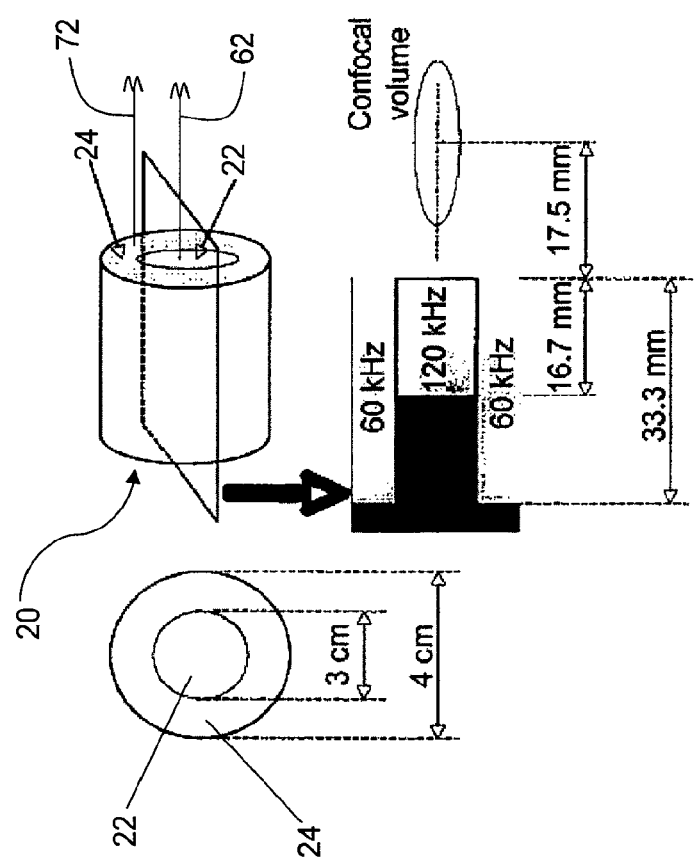
FIG. 2 is a schematic of a dual-element annular array for 120-kHz sonothrombolysis and 60 kHz passive cavitation detection.

As shown in FIGS. 1 and 2, in one aspect of this embodiment, the system for inducing and passively detecting stable cavitation 10 is adapted to provide a determined level of ultrasonic energy and to receive a scattered level of ultrasonic energy substantially throughout the treatment zone of a patient. In one particular aspect, the system for inducing and passively detecting stable cavitation 10 comprises a dual-element annular transducer array 20. The dual-element annular transducer array 20 has a source transducer 22 and a detector transducer 24. The dual-element annular transducer array 20 provides a determined level of ultrasonic energy and receives a scattered level of ultrasonic energy, such that sonothrombolysis and stable cavitation detection may be achieved substantially simultaneously. The size and configuration of the dual-element annular transducer array 20 should be selected so that ultrasound waves, or energy, may be provided substantially throughout the treatment zone of a patient, while avoiding potentially harmful bioeffects such as tissue damage, petechial hemorrhage, blood brain barrier disruption, thermal coagulation, and/or cellular damage to the patient.

The source transducer 22 is adapted to provide a determined level of ultrasonic energy. In one particular aspect, the source transducer 22 has a circular cross-section having a diameter of about 3 centimeters, and the detector transducer 24 has an annular cross-section having an inner diameter of about 3 centimeters and an outer diameter of about 4 centimeters. In another aspect, the detector transducer 24 has a circular cross-section having a diameter of about 3 centimeters, and the source transducer 22 has an annular cross-section having an inner diameter of about 3 centimeters and an outer diameter of about 4 centimeters. However, the dual-element annular transducer array 20 should not be limited to the particular aspects disclosed herein, but may comprise any configuration wherein a source transducer 22 is confocally aligned with a detector transducer 24. Moreover, the source transducer 22 may comprise the annular transducer element surrounding the central circular transducer element, or may comprise the central circular transducer element. Similarly, the detector transducer 24 may comprise the annular transducer element surrounding the central circular transducer element, or may comprise the central circular transducer element.

The source transducer 22 provides an ultrasonic frequency that is a fundamental ultrasonic frequency. Suitable fundamental frequencies produced by the source transducer 22 can range from about 100 kHz to about 10 MHz. In one particular aspect, the source transducer 22 can produce a fundamental ultrasonic frequency of from about 100 kHz to about 2 MHz. In another aspect, the source transducer 22 can produce a fundamental ultrasonic frequency of about 120 kHz.

In one embodiment, the source transducer 22 is configured such that it is adjustable to vary the duty cycle of the ultrasonic energy produced. In one particular aspect, the source transducer 22 is adjustable to vary the duty cycle from about 0.01% to about 100%. Moreover, the source transducer 22 can be configured such that it is adjustable to vary the beamwidth of the ultrasonic energy produced. The beamwidth may be varied such that the source transducer 22 provides a determined level of ultrasonic energy substantially throughout the treatment zone of a patient. In one aspect, the source transducer 22 is configured to provide a beamwidth of about 0.1 centimeters to about 10 centimeters. Additionally, the source transducer 22 can be configured such that it is adjustable to select an ultrasonic pressure amplitude of the ultrasonic energy produced. In a particular aspect, the source transducer 22 is configured to provide an ultrasonic pressure amplitude of from about 0.1 MPa to about 10.0 MPa. In a further aspect, the source transducer 22 is configured to provide an ultrasonic pressure amplitude of from about 0.1 MPa to about 1.0 MPa.

The detector transducer 24 is adapted to receive a scattered level of ultrasonic energy substantially throughout the treatment zone of a patient. In this particular aspect, the detector transducer 24 receives an ultrasonic frequency that is a derivative frequency of the fundamental ultrasonic frequency selected from the group consisting of a subharmonic frequency, an ultraharmonic frequency, and combinations thereof. In this aspect, the detector transducer 24 is configured to receive a bandwidth centered at one or more subharmonic frequency and/or ultraharmonic frequency of the fundamental frequency. In yet another aspect, the detector transducer 24 is configured to receive a bandwidth centered at the subharmonic frequency of about 60 kHz.

Detection of a derivative frequency selected from the group consisting of a subharmonic frequency, an ultraharmonic frequency, and combinations thereof, is indicative of stable cavitation during sonothrombolysis. The scattering of incident wave by ultrasonically activated bubbles on the size scale of nanometers or micrometers occurs at the center frequency and harmonics of the insonifying pulse. However, the presence of half of the fundamental frequency (the subharmonic) and its odd multiples (ultraharmonics) indicate the presence of microbubbles or nanobubbles that are cavitating stably.

As shown in FIGS. 1 and 2, the ultrasonic driver 30 is adapted to generate electrical energy that can be converted at the source transducer 22 to ultrasonic energy suitable for penetrating a treatment zone of a patient. In one aspect, the ultrasonic driver 30 includes a function generator 40, an amplifier 50, and a matching network 60. The ultrasonic driver 30 is electrically connected to the source transducer 22 with a cord 62, such that the system for inducing and passively detecting stable cavitation 10 is adapted to provide a determined level of ultrasonic energy substantially throughout the treatment zone of a patient. The ultrasonic driver 30 may be of a conventional design with an adjustable frequency generator and/or an adjustable power amplifier. The ultrasonic driver 30 should be configured such that the ultrasound waves or energy can be selected to provide a determined level of ultrasonic energy substantially throughout the treatment zone of a patient.

In one embodiment, the function generator 40 is electrically connected to the amplifier 50 with a cord 42. The amplifier 50 amplifies the electrical energy generated by the function generator 40.

In another embodiment, the matching network 60 is electrically connected to the amplifier 50 with a cord 52. The matching network 60 increases the efficiency of the ultrasonic driver 30 by impedance matching circuitry between the amplifier 50 and the source transducer 22. In this particular aspect, the matching network 60 is electrically connected to the source transducer 22 with a cord 62.

The detector transducer 24 converts the scattered level of ultrasonic energy received into an electronic signal. In this particular aspect, the derivative frequency received by the detector transducer 24 comprises a signal. In a further aspect of this particular embodiment, the signal received by the detector transducer 24 is gated. In one embodiment, the signal is filtered such that the detector transducer 24 receives ultrasonic frequencies that are substantially a derivative frequency of the fundamental ultrasonic frequency. In one particular aspect, the derivative frequency of the fundamental frequency received by the detector transducer 24 is selected from the group consisting of a subharmonic frequency, an ultraharmonic frequency, and combinations thereof.

In still another aspect of this embodiment, the system for inducing and passively detecting stable cavitation 10 further comprises a pre-amplifier 70. The pre-amplifier 70 is electrically connected to the detector transducer 24 with a cord 72. The pre-amplifier 70 amplifies the signal received by the detector transducer 24.

In yet another aspect of this embodiment, the system for inducing and passively detecting stable cavitation 10 further comprises a digital oscilloscope 80. The digital oscilloscope 80 is electrically connected to the pre-amplifier 70 with a cord 82. The digital oscilloscope 80 stores the signal amplified by the pre-amplifier 70.

In yet another aspect of this embodiment, the system for inducing and passively detecting stable cavitation 10 further comprises a computer 90. The computer 90 is electrically connected to the digital oscilloscope 80 with a cord 92. The computer 90 acquires the signal stored in the digital oscilloscope 80. The computer 90 provides data acquisition from the signal stored in the digital oscilloscope 80.

In yet still another aspect of this embodiment, the system for inducing and passively detecting stable cavitation 10 further comprises a hydrophone (not shown). The hydrophone is adapted to receive a scattered level of ultrasonic energy substantially throughout the treatment zone of a patient. In a particular aspect, the hydrophone converts the scattered level of ultrasonic energy received into an electronic signal. In this particular aspect, the derivative frequency received by the hydrophone comprises a signal. In a further aspect, the signal received by the hydrophone is gated, such that the hydrophone receives a scattered level of ultrasonic energy that is truncated to receive only signals from a selected distance.

In another embodiment of the present invention, a method for inducing and passively detecting stable cavitation during sonothrombolysis is provided, the method comprising providing a determined level of ultrasonic energy substantially throughout a treatment zone of a patient and detecting a scattered level of ultrasonic energy. The determined level of ultrasonic energy is produced by a source transducer 22 and comprises a fundamental ultrasonic frequency. The scattered level of ultrasonic energy is received by a detector transducer 24 and comprises a derivative frequency of the fundamental ultrasonic frequency selected from the group consisting of a subharmonic frequency, an ultraharmonic frequency, and combinations thereof, wherein detection of the derivative frequency is indicative of stable cavitation during sonothrombolysis.

The method for passively detecting stable cavitation comprises providing a determined level of ultrasonic energy substantially throughout a treatment zone of a patient, wherein the determined level of ultrasonic energy is produced by a source transducer 22, and detecting a scattered level of ultrasonic energy, wherein the scattered level of ultrasonic energy is received by a detector transducer 24. In one particular aspect, the source transducer 22 and the detector transducer 24 comprise a dual-element annular transducer array 20. In a further aspect, the source transducer 22 has a circular cross-section having a diameter of about 3 centimeters, and the detector transducer 24 has an annular cross-section having an inner diameter of about 3 centimeters and an outer diameter of about 4 centimeters. In another aspect, the detector transducer 24 has a circular cross-section having a diameter of about 3 centimeters, and the source transducer 22 has an annular cross-section having an inner diameter of about 3 centimeters and an outer diameter of about 4 centimeters. However, the dual-element annular transducer array 20 may comprise any configuration wherein the source transducer 22 is confocally aligned with the detector transducer 24.

The method also comprises providing a determined level of ultrasonic energy substantially throughout the treatment zone of a patient, wherein the determined level of ultrasonic energy is produced by a source transducer 22. The determined level of ultrasonic energy is produced by a source transducer 22 and comprises a fundamental ultrasonic frequency. Suitable fundamental frequencies produced by the source transducer 22 can be, for example, from about 100 kHz to about 10 MHz. In one particular aspect, the source transducer 22 can produce a fundamental ultrasonic frequency from about 100 kHz to about 2 MHz. In another aspect, the source transducer 22 can produce a fundamental ultrasonic frequency of about 120 kHz.

In another aspect, the source transducer 22 is configured such that it is adjustable to vary the Rayleigh distance to assist in concentrating or directing ultrasound waves or energy to the treatment zone so that ultrasound waves or energy may be provided substantially throughout the treatment zone of a patient. In one particular aspect, the ultrasonic energy is emitted from the source transducer 22 with a Rayleigh distance from about 0.1 centimeters to about 30 centimeters. In a further aspect, the ultrasonic energy is emitted from the source transducer 22 with a Rayleigh distance from about 0.1 centimeters to about 10 centimeters. Moreover, the source transducer 22 is configured such that it is adjustable to vary the beamwidth of the ultrasonic energy produced. The beamwidth may be varied such that the source transducer 22 provides a determined level of ultrasonic energy substantially throughout the treatment zone of a patient. In one aspect, the source transducer 22 is configured to provide a beamwidth of about 0.1 centimeter to about 10 centimeters.

The method also comprises detecting a scattered level of ultrasonic energy, wherein the scattered level of ultrasonic energy is received by a detector transducer 24. The scattered level of ultrasonic energy is received by the detector transducer 24 and comprises a derivative frequency of the fundamental ultrasonic frequency selected from the group consisting of a subharmonic frequency, an ultraharmonic frequency, and combination thereof. In one specific aspect, the detector transducer 24 detects a subharmonic frequency of the fundamental ultrasonic frequency of about 60 kHz. As previously discussed, detecting a derivative frequency selected from the group consisting of a subharmonic frequency, an ultraharmonic frequency, and combinations thereof, is indicative of stable cavitation during sonothrombolysis as the presence of half of the fundamental frequency (the subharmonic) and its odd multiples (ultraharmonics) indicate the presence of microbubbles or nanobubbles that are cavitating stably.

In yet still another aspect of this embodiment, the method for passively detecting stable cavitation further comprises detecting the scattered level of ultrasonic energy with a hydrophone.

In still another embodiment, a method for enhancing stable cavitation during sonothrombolysis is provided, the method comprising administering a nucleating agent and a thrombolytic agent to a treatment zone of a patient and providing a determined level of ultrasonic energy substantially throughout the treatment zone of the patient. The determined level of ultrasonic energy is produced by a source transducer and comprises a fundamental ultrasonic frequency, wherein the determined level of ultrasonic energy is provided in intervals separated by rest periods, wherein substantially no ultrasonic energy is provided during rest periods, such that the intervals of the determined level of ultrasonic energy enhance stable cavitation during sonothrombolysis.

In a further aspect, the method of enhancing stable cavitation further comprises detecting a scattered level of ultrasonic energy. The scattered level of ultrasonic energy is received by a detector transducer and comprises a derivative frequency of the fundamental ultrasonic frequency selected from the group consisting of a subharmonic frequency, an ultraharmonic frequency, and combinations thereof.

The method of enhancing stable cavitation comprises administering a nucleating agent to a treatment zone of a patient. The nucleating agent initiates cavitation, and any agent capable of initiating cavitation may be used. In one aspect, the nucleating agent is gas bubbles stabilized against dissolution in a fluid. In a further aspect, the nucleating agent is a gas releasably contained by a protective material.

The protective material is configured to allow the nucleating agent to be released when exposed to a determined level of ultrasonic energy; in one aspect, the protective material is capable of being ruptured by ultrasonic energy generated by the source transducer 22. The protective material is also configured to allow circulation of the encapsulated nucleating agent throughout the patient. Suitable protective materials include, but are not limited to, lipids and/or liposomes. Liposomes can entrap microbubbles and nanobubbles, enabling enhanced echogenicity and cavitation nucleation. In one particular aspect, the liposome is an echogenic liposome ("ELIP").

Echogenic liposomes can be targeted to certain tissues by attaching specific peptides, ligands, or antibodies to the surface of the liposome. Additionally, echogenic liposomes may be fragmented with ultrasound near a target tissue. In one specific aspect, echogenic liposomes can be targeted with peptides or ligands to bind to receptors characteristic of intravascular diseases (or blood clots). Targeting echogenic liposomes enables selective accumulation of the nucleating agent to a specific area. In one particular aspect, echogenic liposomes could be targeted to a treatment area comprising a blood clot.

In another aspect, the nucleating agent may be selected from the group consisting of nanobubbles, microbubbles, and ultrasound contrast agents. In one embodiment, ultrasound contrast agents act as cavitation nuclei at the site of a blood clot. Moreover, infusions of ultrasound contrast agents may sustain the gentle bubble activity that is indicative of stable cavitation. In one specific aspect, the ultrasound contrast agent is perflutren-lipid microspheres, or Definity® (Lantheus Medical Imaging, N. Billerica, Mass.).

The method of enhancing stable cavitation also comprises administering a thrombolytic agent to a treatment zone of a patient. In one aspect, the thrombolytic agent may comprise tissue plasminogen activator ("t-PA"); t-PA is a protein manufactured by vascular endothelial cells that regulates clot breakdown in the body. t-PA can be manufactured using recombinant biotechnology techniques. W. F. Bennett & D. L. Higgins, *Tissue Plasminogen Activator: The Biochemistry and Pharmacology of Variants Produced by Mutagenesis,* 30 Annual Review of Pharmacology and Toxicology 91, 91-121 (1990). Additional examples of thrombolytic agents include, but are not limited to, recombinant tissue plasminogen activator ("rt-PA"), streptokinase, urokinase, and tenecteplase.

The method of enhancing stable cavitation also comprises providing a determined level of ultrasonic energy substantially throughout the treatment zone of a patient. In one aspect, the determined level of ultrasonic energy is produced by a source transducer 22 and comprises a fundamental ultrasonic frequency. In one particular aspect, the source transducer 22 may be a single element transducer, a linear array transducer, or a two-dimensional array transducer. In a further aspect, the source transducer 22 may have a circular cross-section having a diameter of about 3 centimeters.

Figure 3:
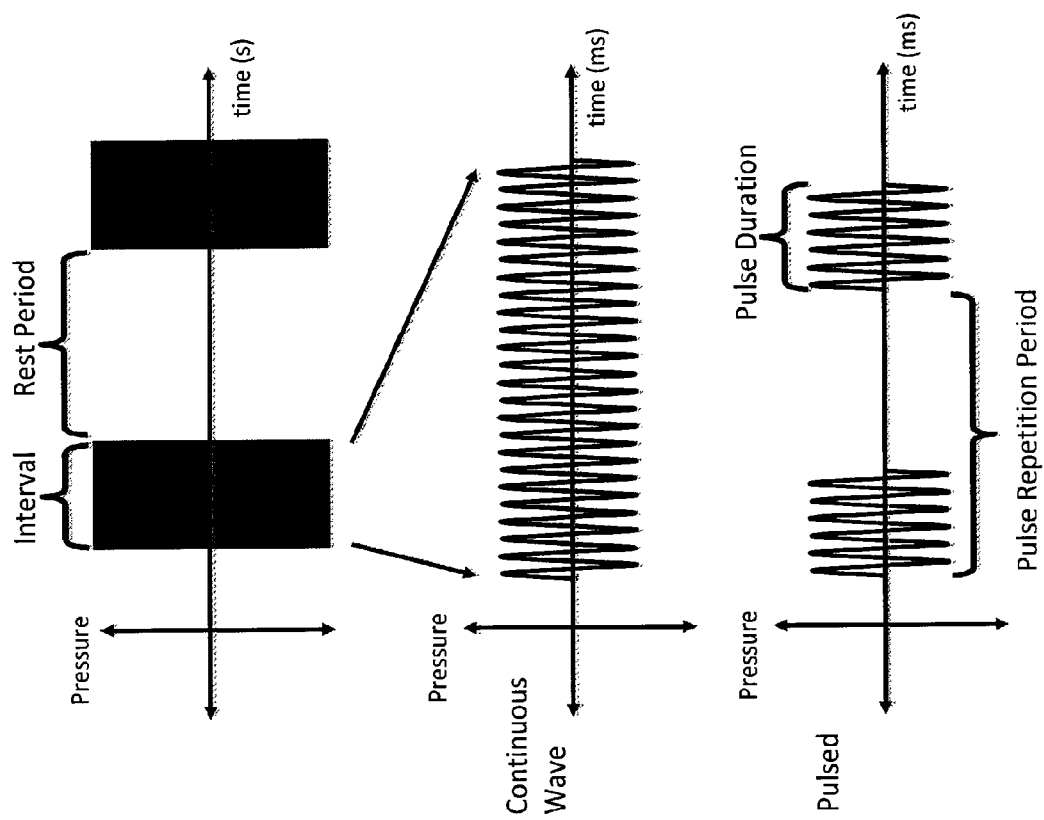
FIG. 3 is a schematic of the determined level of ultrasonic energy being provided in intervals separated by rest periods, wherein substantially no ultrasonic energy is provided during the rest periods. The interval includes either continuous wave or pulsed wave ultrasound activity of the source transducer; the rest period is a quiescent period. The interval duration is determined by assessing the duration of stable cavitation and the rest period duration is selected to allow the in-flow of a nucleating agent or an ultrasound contrast agent.

In yet another aspect, the source transducer 22 is configured such that it is adjustable to vary the Rayleigh distance, natural focus, or focus to assist in concentrating or directing ultrasound waves or energy to the treatment zone so that ultrasound waves or energy may be provided substantially throughout the treatment zone of a patient. In a further aspect, the ultrasonic energy may be emitted from the source transducer 22 with a Rayleigh distance, natural focus, or focus of from about 0.1 cm to about 30 cm. In still a further aspect, the ultrasonic energy may be emitted from the source transducer 22 with a Rayleigh distance, natural focus, or focus of from about 0.1 cm to about 10 cm. As shown in FIG. 3, the determined level of ultrasonic energy produced by a source transducer 22 is provided in intervals separated by rest periods, wherein substantially no ultrasonic energy is provided during the rest periods. The interval comprises either continuous wave or pulsed wave ultrasound produced by the source transducer 22; the rest period comprises a quiescent period. The interval duration is dictated by the duration of stable cavitation and the rest period duration is dictated by the in-flow of the nucleating agent or ultrasound contrast agent.

The determined level of ultrasonic energy is provided in intervals to enhance stable cavitation. By providing a determined level of ultrasonic energy in intervals separated by rest periods, the nucleating agent is enabled to flow into the treatment zone of the patient. The bubble activity that elicits subharmonic frequencies, ultraharmonic frequencies, and combinations thereof, may be sustained using an intermittent or continuous infusion of a commercial contrast agent; thus, providing a determined level of ultrasonic energy in intervals separated by rest periods allows the nucleating agent to flow into the treatment zone of the patient and enhances stable cavitation.

In one aspect of this embodiment, the determined level of ultrasonic energy is provided for an interval duration of from about 10 milliseconds to about 5 minutes. In a further aspect, the determined level of ultrasonic energy is provided for an interval duration of from about 10 milliseconds to about 10 seconds. In still a further aspect, the determined level of ultrasonic energy is provided for an interval duration of about 8.5 seconds. In yet another aspect of this embodiment, the rest period duration is from about 1 second to about 5 minutes. In a further aspect, the rest period duration is from about 1 second to about 60 seconds. In a more specific aspect, the rest period duration is from about 1 second to about 30 seconds. In a very specific aspect, the rest period duration is about 19 seconds.

The source transducer 22 provides a determined level of ultrasonic energy substantially throughout the treatment zone of a patient, wherein the determined level of ultrasonic energy is produced by a source transducer 22 and comprises a fundamental ultrasonic frequency. The determined level of ultrasonic energy may comprise pulsed wave or continuous wave ultrasound. Suitable fundamental frequencies produced by the source transducer 22 include frequencies from about 100 kHz to about 10 MHz. In one particular aspect, the source transducer 22 produces a fundamental ultrasonic frequency from about 100 kHz to about 2 MHz. In another aspect, the treatment zone comprises a clot and the source transducer 22 produces a fundamental ultrasonic frequency of about 120 kHz.

Figure 4:
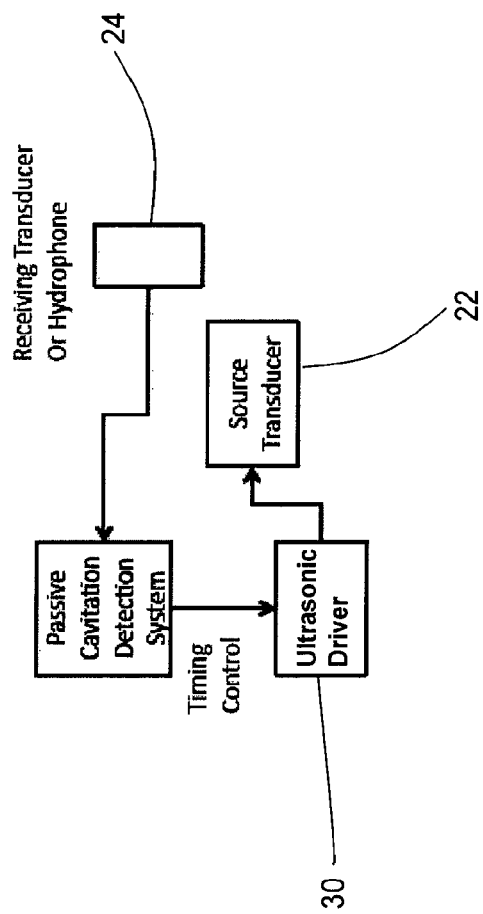
FIG. 4 is a block diagram of a passive stable cavitation detection and control system for ultrasound-enhanced thrombolysis.

As shown in FIG. 4, in another aspect, the method of enhancing stable cavitation further comprises detecting a scattered level of ultrasonic energy. The scattered level of ultrasonic energy is received by a detector transducer 24 and comprises a derivative frequency of the fundamental frequency selected from the group consisting of a subharmonic frequency, an ultraharmonic frequency, and combinations thereof. In one aspect, the scattered level of ultrasonic energy is received by a passive cavitation detector. In a further aspect, the passive cavitation detector is selected from the group consisting of a hydrophone, a detector transducer, and a passive transducer array.

In a further aspect of this embodiment, the method of enhancing stable cavitation further comprises adjusting the determined level of ultrasonic energy produced by the source transducer 22 in accordance with the detected scattered level of ultrasonic energy received by a passive cavitation detector. By monitoring the detected scattered level of ultrasonic energy received by a passive cavitation detector, stable cavitation may be. In response to monitoring stable cavitation, the source transducer 22 may be adjusted to provide a modified determined level of ultrasonic energy; additionally, in response to monitoring stable cavitation, the interval duration and rest period duration may also be modified to allow inflow of the nucleating agent. For example, if the scattered level of ultrasonic energy received by the passive cavitation detector indicates continued bubble activity, the source transducer 22 remains on. In a further example, if the scattered level of ultrasonic energy received by the passive cavitation detector decreases or if cavitation is not detected, a rest period is initiated to allow the nucleating agent to flow into the treatment zone. In a specific embodiment, when the scattered level of ultrasonic energy of the derivative frequency drops below about twice the background noise level in the passive cavitation detection system, a rest period is initiated.

In one particular aspect of this embodiment, the treatment zone comprises a blood clot and thrombolysis is enhanced substantially throughout the treatment zone. In one embodiment, enhanced thrombolysis includes percent clot mass loss of about 20% to about 500% greater than that observed without the provision of ultrasound. See, for example, FIG. 5, wherein the percent clot mass lost is greater than about 80%±1% standard deviation wherein a blood clot is treated with rt-PA, Definity®, and ultrasound; in contrast, the percent clot mass loss is less than about 35%±1% standard deviation wherein the blood clot is treated with rt-PA and Definity®, wherein substantially no ultrasound is provided.

It will be appreciated that the system and methods disclosed herein are useful in sonothrombolysis. Additionally, it will be appreciated that the system and methods disclosed herein are useful in the treatment of thrombo-occlusive diseases including but not limited to stroke, pulmonary emboli, myocardial infarction, deep vein thrombosis, and/or arteriovenous fistula thrombosis. Moreover, it will be appreciated that ultrasound-mediated enhancement of stable cavitation increases thrombolysis substantially throughout the treatment zone.

EXAMPLES

The following non-limiting examples illustrate the methods and systems of the present invention.

Example 1

Passive Cavitation Detection with Dual Element Annular Array

Figure 6:
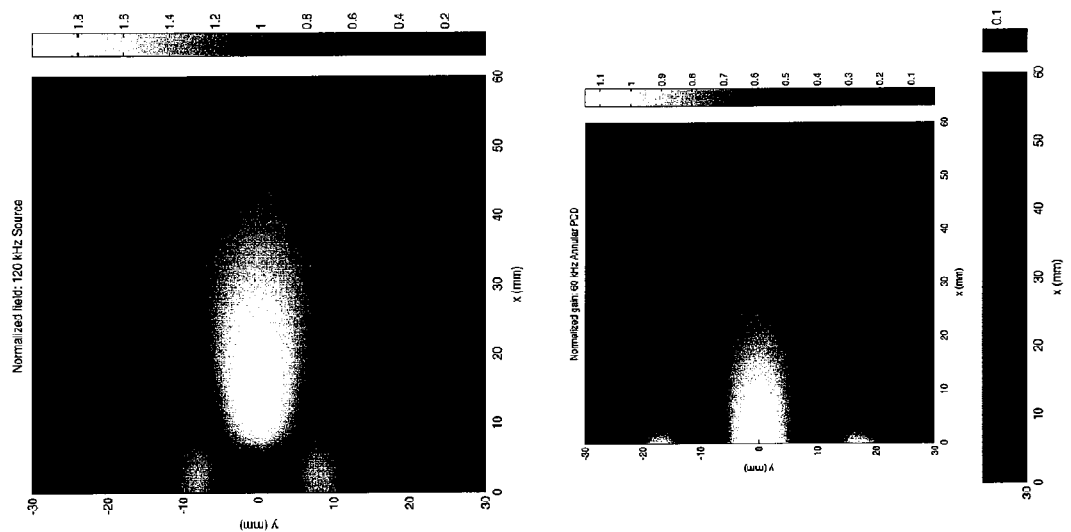
FIG. 6 illustrates the computed cross-sectional beam pattern for a 120 kHz unfocused source transducer and surrounding annular 60 kHz passive cavitation detector.

Dual Element Annular Array for 120-kHz Sonothrombolysis and 60-kHz Passive Cavitation Detection. A dual element annular array (FIG. 1) was designed to enable inducing and passively detecting stable cavitation during sonothrombolysis. To test the feasibility of this design approach, acoustic radiation from the 3 cm, 120-kHz source was computed using an exact series solution for the field of a baffled circular radiator in a homogeneous medium. Using the same method, the spatial sensitivity pattern of the surrounding annular passive cavitation detector (inner diameter 3 cm, outer diameter 4 cm) was computed at the subharmonic frequency of 60 kHz. Cross sections of the beam patterns are shown in FIG. 6. The field of the 120-kHz source had a −6 dB depth of field of 46 mm and a −6 dB beamwidth of 1.4 cm. The annular broadband passive cavitation detector had a collimated beam with amplitude 0.84 (−1.5 dB relative to surface excitation) and a beamwidth of 1.6 cm at the Rayleigh distance of the 120 kHz source. The results demonstrated that both uniform sonication and passive cavitation detection may be achieved over the entire region of interest containing a blood clot.

Assessment of Dual Element 120-kHz/60-kHz Array Beam Distortion. Acoustic field profiles of the prototype array output were performed. An omnidirectional hydrophone was mounted on a computer-controlled microposing system to scan the interior of human and pig skulls. The penetration of ultrasound (both 120 kHz and 60 kHz) was through the temporal and frontal bones for the human and the pig skulls, respectively.

Passive Cavitation Detection. A broadband passive cavitation detector (PCD) was employed to detect cavitating micron-sized bubbles. A dual element 120-kHz/60-kHz array transducer was used as a passive cavitation detector with porcine blood clots in an ex vivo porcine carotid artery model. The 60-kHz confocal annulus (Sonic Concepts, Inc., Woodburn, Wash.) was employed to detect cavitation activity passively in the sample volume as shown in FIG. 2. The dual element array transducer was mounted on a micrometer-controlled 3-axis translation stage (Newport 423, Irvine, Calif., USA) for precise alignment with the blood clots. Moreover, as shown in FIG. 6, the detector transducer 24 enables monitoring of stable cavitation along the entire volume of the clot.

Detected Signal Analysis. Signals acquired by the PCD were gated to account for travel time of the pulse from the 120-kHz transducer to the clot and back to the 60 kHz element. The signal received by the PCD was amplified using a pre-amplifier (Signal Recovery 5185, Oak Ridge, Tenn., USA) and stored using a digital oscilloscope (LeCroy Waver Surfer 424, Chestnut Ridge, N.Y., USA). The acquired signal by the PCD was also gated to ensure that cavitation was monitored over a region encompassing the entire clot and surrounding fluid. The squared frequency spectra of received pulses was processed in the frequency domain.

Acoustic Pressure Threshold Determination. Using the PCD, the acoustic pressure threshold of stable and inertial cavitation at 120 kHz was determined in an ex vivo porcine carotid artery flow model with 1) plasma alone, and 2) rt-PA and Definity® in the flowing plasma. Porcine whole blood clots were placed in excised, living porcine carotid arteries through which porcine plasma flowed and were maintained in a 37° C. temperature-controlled water bath. The peak rarefactional pressure amplitude was increased slowly until initially stable and then inertial cavitation was detected by the PCD. The lowest peak rarefactional pressure amplitude which yielded stable and inertial cavitation was recorded as the threshold pressure for each fluid.

Example 2

Effects of Stable Cavitation on Thrombolysis

Cavitation Nucleation with Infusion of Contrast Agent in an In Vitro Human Clot Model. An approach for inducing cavitation using infusion of a contrast agent, Definity®, was tested experimentally in vitro. Human whole blood clots and rt-PA (96 µg/ml) were placed in human fresh frozen plasma in a thin-walled latex sample holder which was placed in a tank of water at 37° C. Percent clot mass loss was assessed as a function of peak-to-peak acoustic pressure for the following treatments: (a) no rt-PA, no Definity®, no pulsed ultrasound (the control); (b) rt-PA alone; (c) rt-PA, Definity® infusions, and pulsed ultrasound (~0.12 MPa peak-to-peak pressure amplitude); (d) rt-PA, Definity® infusions, and pulsed ultrasound (~0.21 MPa peak-to-peak pressure amplitude); (e) no rt-PA, Definity® infusions, and pulsed ultrasound (~0.32 MPa peak-to-peak pressure amplitude); (f) rt-PA, phosphate buffered saline infusions (no Definity®) and pulsed ultrasound (~0.32 MPa peak-to-peak pressure amplitude); and (g) rt-PA, Definity® infusions, and pulsed ultrasound (~0.32 MPa peak-to-peak pressure amplitude). A sample size of six was used for each treatment. Human whole blood clots, when exposed to stable cavitation activity in the presence of rt-PA, resulted in the highest mass loss of 26.0±4%.

Sonothrombolysis Transducer. A single-element 120-kHz source transducer was operated in pulsed mode over a range of peak-to-peak pressure amplitudes, with an 80% duty cycle, and 1667 Hz pulse repetition frequency. The peak-to-peak pressure amplitudes were selected such that no cavitation (~0.12 MPa and ~0.21 MPa), or stable cavitation (~0.32 MPa) was induced.

Stable Cavitation Detection. Stable cavitation was detected using a focused polyvinylidine difluoride (PVDF) hydrophone immersed in the tank of water aligned confocally with the sonothrombolysis transducer.

Tracking Emissions to Obtain Feedback. Stable cavitation was monitored by tracking the ultraharmonic emissions during the combined ultrasound and thrombolytic exposures in the in vitro human blood clot model. Cavitation activity was monitored by tracking subharmonic and ultraharmonic emissions during the treatment. The emission's energy was integrated over time as a metric for the amount of stable cavitation. A significant correlation was observed between clot mass loss and ultraharmonic signals ($r=0.8549$, $p<0.0001$, $n=24$).

Promotion of Stable Cavitation with Ultrasound Contrast Agent. A dual antibody immunofluorescence technique was employed to measure penetration depths of rt-PA and plasminogen into the clots. The largest mean penetration depth of rt-PA (222 μm) and plasminogen (241 μm) was observed in the presence of stable cavitation activity. Thus, it was demonstrated that a contrast agent can be used to nucleate cavitation and can result in a desired therapeutic effect.

A contrast agent, Definity®, was successfully used to promote and sustain the nucleation of stable cavitation during pulsed ultrasound exposure at 120 kHz for 30 minutes. The largest percent clot mass loss of 26.2±2.6% was observed in human whole blood clots in the presence of sustained stable cavitation activity.

Model Thresholds for Bubble Activity vs. Bubble Size to Determine Optimal Size. The minimum inertial cavitation threshold estimated by the microbubble response was observed at the resonance size of the microbubble for all the frequencies studied. The minimum inertial cavitation threshold increased with increasing frequency. The range of bubble sizes that may cavitate stably decreases at higher frequencies. This suggested that higher frequencies would require the optimum sized nucleus to be present for generating stable cavitation.

Example 3

Effects of Stable Cavitation on Thrombolysis in an Ex Vivo Porcine Artery Model with Interval Ultrasound Ex Vivo Porcine Carotid Artery Model with Physiologic Flows and Pressures. Porcine whole blood clots were inserted into living, excised porcine carotid arteries, and kept viable in a thin-walled latex chamber filled with degassed artificial cerebrospinal fluid while oxygenated plasma flowed through the lumen. The chamber was placed in a tank containing degassed filtered water at 37° C. A series of experiments were performed by infusing 1 ml/min plasma with 0.31 μl Definity® per 1 ml plasma through a porcine artery filled with a porcine whole blood clot at a physiologic pressure of 100±15 mmHg. Each clot and artery were insonated with 120 kHz continuous wave ultrasound at peak-to-peak pressures ranging from 0.37 MPa to 0.54 MPa for 45 seconds. The signals were analyzed for stable and inertial cavitation power.

Ultrasound Source Transducer and Passive Cavitation Detector. A single-element transducer operating at 120 kHz was used to insonate the porcine clots in living, excised porcine carotid arteries. A 2.25-MHz center frequency transducer was used as a passive cavitation detector to receive acoustic signals scattered from within the vessel. These signals were digitized and converted to power spectra.

To detect stable cavitation, the power spectra at ultraharmonic frequencies (from 300 kHz to 3.8 MHz) of the fundamental frequency was accumulatively summed over the treatment period to yield a total stable cavitation dose. In a similar manner, inertial cavitation was detected by summing the power spectra at frequencies between the harmonic frequencies and ultraharmonic frequencies (from 300 kHz to 3.8 MHz) of the fundamental frequency. More particularly, the power spectra was accumulatively summed over the treatment period to yield an inertial cavitation dose.

Figure 7:
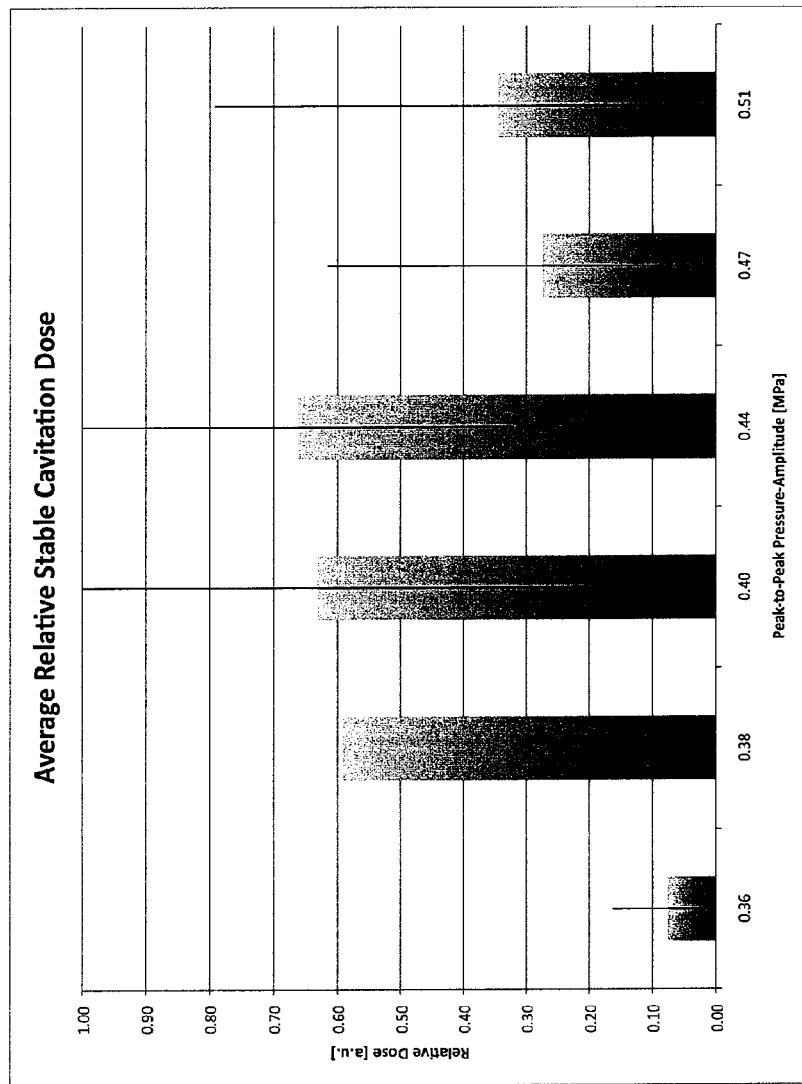
FIG. 7 is a graph illustrating the average relative stable cavitation dose in the ex vivo porcine carotid artery model with physiologic flows and pressures. The stable cavitation dose was measured over a range of peak-to-peak acoustic pressures within a living, excised porcine carotid artery and was normalized by the maximum stable cavitation dose within that vessel to yield a relative dose in arbitrary units. Error bars represent the standard deviation. This data indicates a peak-to-peak pressure amplitude of about 0.44 MPa yields the largest stable cavitation dose on average.

Pressure Determination. An "optimal" peak-to-peak pressure output was selected based on maximizing the amount of stable cavitation ("the dose") taking into account variable on- and off-times (i.e. intervals and rest periods, respectively). FIG. 7 is a graph illustrating the average relative stable cavitation dose in the ex vivo porcine carotid artery model with physiologic flows and pressures. The stable cavitation dose was measured over a range of peak-to-peak acoustic pressures within a living, excised porcine carotid artery and was normalized by the maximum stable cavitation dose within that vessel to yield a relative dose in arbitrary units. Error bars represent the standard deviation. The data indicate that the peak-to-peak pressure amplitude of about 0.44 MPa gave the largest stable cavitation dose on average.

Figure 9:
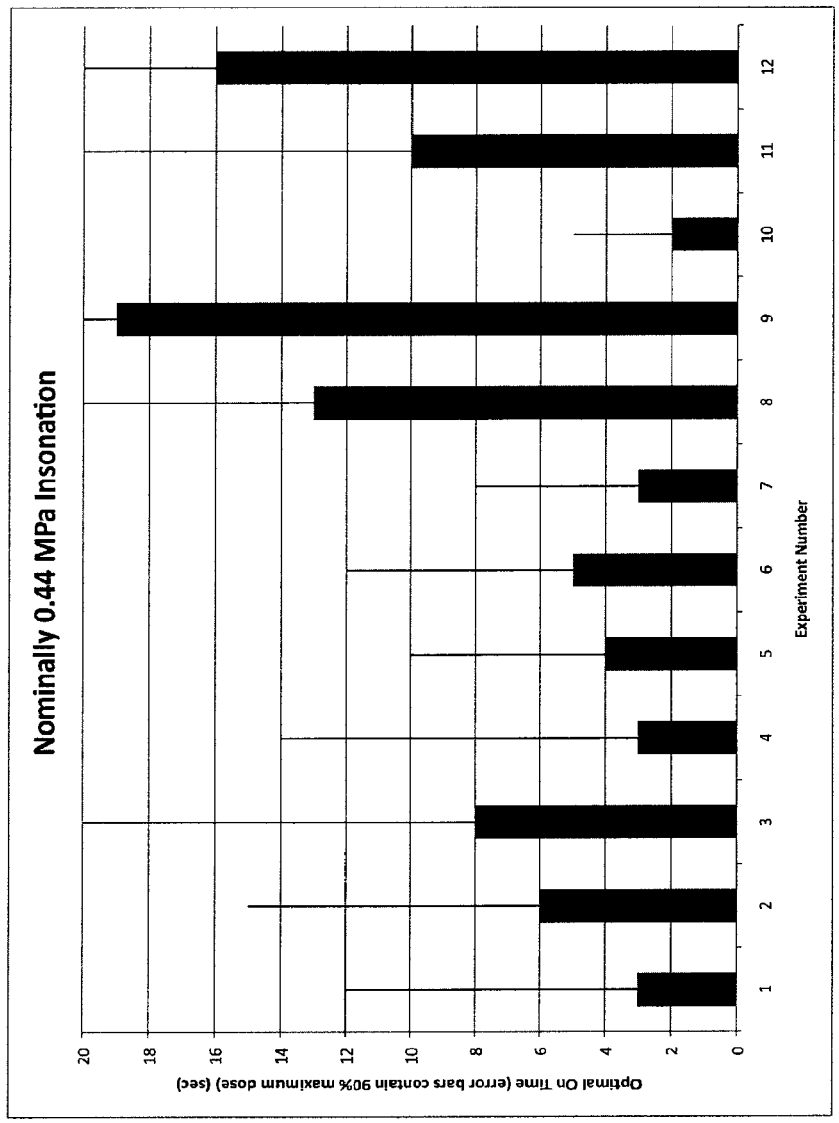
FIG. 9 is a graph illustrating optimization of on-time ultrasound in the ex vivo porcine carotid artery model with physiologic flows and pressures. For a selected pressure (about 0.44 MPa), twelve trials are shown with the optimal on-time for each trial shown in blue with the error bars extending to the 90% of optimal on-time. The optimal on-time is the time for which a 30 minute trial would give the maximum cavitation dose.

Optimization of Ultrasound Duration. The duration of ultrasound on-time was optimized for the particular peak-to-peak pressure amplitude yielding the largest average stable cavitation dose. As shown in FIG. 8 (left), stable cavitation activity was recorded passively as a function of time. As shown in FIG. 8 (right), the total stable cavitation dose during a treatment period was calculated as a function of the ultrasound on-time. The on-time yielding the maximum total stable cavitation dose was considered to be optimal on-time to promote sonothrombolysis. The optimal on-time is shown in FIG. 9 for twelve experiments in the ex vivo porcine carotid artery model with physiologic flows and pressures. The error bars extend over the times that yielded at least 90% of the maximum stable cavitation dose. The mean of these optimal on-time values was 8.5 seconds and this on-time value was used for subsequent sonothrombolysis experiments, shown in FIG. 5.

Clot Mass Loss with Treatment. A second series of experiments were performed to determine the thrombolytic efficacy of ultrasound-enhanced thrombolysis using the optimized interval ultrasound exposure in the ex vivo porcine carotid artery model with physiologic flows and pressures. The pressure was 100±15 mmHg and the mean flow velocity was 2.7±1.8 ml/min. The ultrasound insonation parameters were 120-kHz center frequency and 0.44 MPa peak-to-peak pressure amplitude for 8.5 seconds and a rest period over a 30 minute treatment period. The rest periods were employed within a pulsing sequence to allow the contrast agent to entirely refill the target volume. Treatments included: 1) plasma alone, 2) plasma and 3.15 μl rt-PA/ml plasma, 3) plasma with interval ultrasound, 4) plasma with 3.15 μl/ml rt-PA and 0.31 μl/ml Definity® microbubble contrast agent, 5) plasma with 3.15 μl/ml rt-PA and interval ultrasound, and 6) plasma with 3.15 μ/ml rt-PA, 0.31 μl/m1 Definity®, and interval ultrasound. Clots were weighed before and after treatment to yield percent clot mass loss.

Figure 5:
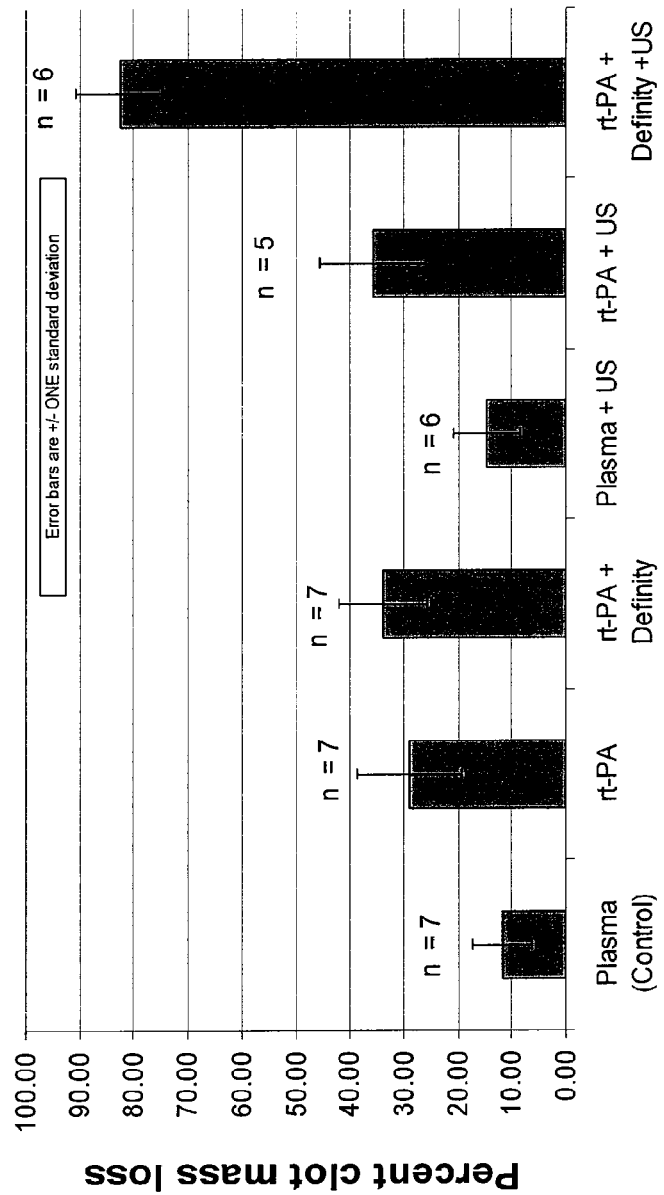
FIG. 5 is a graph illustrating clot mass loss with treatment in an ex vivo porcine carotid artery model with physiologic flows and pressures of 0-8 ml/min and 80-120 mmHg, respectively.

FIG. 5 shows the mean clot mass loss for each treatment in the vascular model, with vertical error bars representing±one standard deviation. A two-way analysis of variance ("ANOVA") with repeated measurements revealed that there were significant differences in mass loss among arteries perfused with the mixture rt-PA and Definity® and those perfused with plasma alone, with and without ultrasound ($F=60.5$, $p<0.0001$). The ANOVA further showed that the effects of rt-PA with Definity® interact significantly with the effects of ultrasound.

This phenomenon was further studied with four paired t-tests (two-tailed). To keep the overall level of significance at 0.05, each individual t-test was performed with an alpha of 0.0125 (0.05/4) in order to be considered significant. With ultrasound, there was a difference between groups with and without rt-PA with Definity® ($p<0.0001$), and for those arteries exposed to ultrasound and those arteries which were not (p<0.0001). In the absence of ultrasound, rt-PA with Definity® produces a significantly higher mass loss than plasma alone (p=0.0001). With no rt-PA or Definity® present, however, the effect of ultrasound was not significant (p=0.19). A follow-up student's t-test showed no difference between rt-PA-treated arteries with or without Definity® and without ultrasound.

It is noted that terms like "preferably," "generally," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

All documents cited are incorporated herein by reference; the citation of any document is not to be construed as an admission that it is prior art with respect to the present invention.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. A method for enhancing stable cavitation during sonothrombolysis, comprising:
   administering a nucleating agent and a thrombolytic agent to a target treatment zone of a patient;
   providing a determined level of ultrasonic energy throughout the target treatment zone of the patient, wherein the determined level of ultrasonic energy is produced by a source transducer and comprises a fundamental ultrasonic frequency, wherein the determined level of ultrasonic energy is provided in intervals separated by rest periods, each interval lasting for an interval duration and each rest period lasting for a rest period duration, wherein no ultrasonic energy is provided during the rest periods;
   detecting a scattered level of ultrasonic energy with a detector transducer, wherein the scattered level of ultrasonic energy is received by the detector transducer and comprises a derivative frequency of the fundamental ultrasonic frequency selected from the group consisting of a subharmonic frequency, an ultraharmonic frequency, and combinations thereof; and
   modifying the intervals and rest periods to maintain stable cavitation by leaving the source transducer on when scattered ultrasonic waves of the derivative frequency are detected, and initiating a rest period when scattered ultrasonic waves of the derivative frequency decrease or are not detected.

2. The method of enhancing stable cavitation of claim 1, wherein the ultrasonic energy is emitted from the source transducer with a Rayleigh distance of from about 0.1 cm to about 30 cm.

3. The method of enhancing stable cavitation of claim 1, wherein an interval of ultrasonic energy comprises pulsed wave or continuous wave ultrasound.

4. The method of enhancing stable cavitation of claim 1, wherein the interval duration is from about 10 milliseconds to about 5 minutes.

5. The method of enhancing stable cavitation of claim 4, wherein the interval duration is about 8.5 seconds.

6. The method of enhancing stable cavitation of claim 1, wherein the rest period duration is from about 1 second to about 5 minutes.

7. The method of enhancing stable cavitation of claim 6, wherein the rest period duration is about 19 seconds.

8. The method of enhancing stable cavitation of claim 1, wherein the source transducer produces a fundamental ultrasonic frequency of from about 100 kHz to about 10 MHz.

9. The method of enhancing stable cavitation of claim 8, wherein the source transducer produces a fundamental ultrasonic frequency of from about 100 kHz to about 2 MHz.

10. The method of enhancing stable cavitation of claim 1, wherein the treatment zone comprises a clot and the source transducer produces a fundamental ultrasonic frequency of about 120 kHz.

11. The method of enhancing stable cavitation of claim 1, wherein the nucleating agent is selected from the group consisting of nanobubbles, microbubbles, and ultrasound contrast agents.

12. The method of enhancing stable cavitation of claim 1, wherein the administering a nucleating agent comprises administering perflutren-lipid micro spheres.

13. The method of enhancing stable cavitation of claim 1, wherein the step of administering a nucleating agent comprises administering a gas releasably contained by a protective material that allows the nucleating agent to be released when exposed to a determined level of ultrasonic energy.

14. The method of enhancing stable cavitation of claim 1, wherein the step of administering a nucleating agent comprises administering a gas releasably contained by a liposome that allows the nucleating agent to be released when exposed to a determined level of ultrasonic energy.

15. The method of enhancing stable cavitation of claim 1, wherein the step of administering a nucleating agent comprises administering a gas releasably contained by an echogenic liposome that allows the nucleating agent to be released when exposed to a determined level of ultrasonic energy.

16. The method of enhancing stable cavitation of claim 1, wherein the treatment zone comprises a blood clot and thrombolysis is enhanced throughout the treatment zone.

* * * * *

UNITED STATES PATENT AND TRADEMARK OFFICE
CERTIFICATE OF CORRECTION

PATENT NO. : 9,675,820 B2
APPLICATION NO. : 15/008821
DATED : June 13, 2017
INVENTOR(S) : Christy K. Holland et al.

Page 1 of 1

It is certified that error appears in the above-identified patent and that said Letters Patent is hereby corrected as shown below:

In the Specification

Column 1 Line 12 please insert the following paragraph:
--FEDERALLY SPONSORED RESEARCH OR DEVELOPMENT
This invention was made with government support under R01 NS047603 awarded by National Institutes of Health. The government has certain rights in the invention.--

Signed and Sealed this
Twenty-fourth Day of December, 2019

Andrei Iancu
*Director of the United States Patent and Trademark Office*